United States Patent [19]

Craig et al.

[11] Patent Number: 4,480,042

[45] Date of Patent: * Oct. 30, 1984

[54] COVALENTLY BONDED HIGH REFRACTIVE INDEX PARTICLE REAGENTS AND THEIR USE IN LIGHT SCATTERING IMMUNOASSAYS

[75] Inventors: Alan R. Craig; William A. Frey; Charles C. Leflar; Catharine E. Looney, all of Wilmington, Del.; Michael A. G. Luddy, West Chester, Pa.

[73] Assignee: E. I. Du Pont de Nemours and Company, Wilmington, Del.

[*] Notice: The portion of the term of this patent subsequent to Aug. 30, 2000 has been disclaimed.

[21] Appl. No.: 495,621

[22] Filed: May 18, 1983

Related U.S. Application Data

[63] Continuation-in-part of Ser. No. 315,922, Oct. 28, 1981, Pat. No. 4,401,765, which is a continuation-in-part of Ser. No. 298,473, Sep. 1, 1981, abandoned.

[51] Int. Cl.[3] ............................................. G01N 33/54

[52] U.S. Cl. .................................... 436/533; 436/500; 436/805; 436/815

[58] Field of Search ................ 436/533, 500, 805, 815

[56] References Cited

U.S. PATENT DOCUMENTS

| | | |
|---|---|---|
| 4,064,080 | 12/1977 | Daniel et al. . |
| 4,166,102 | 8/1979 | Johnson . |
| 4,181,636 | 1/1980 | Fischer . |
| 4,210,723 | 7/1980 | Dorman et al. . |
| 4,226,747 | 10/1980 | Roncari . |
| 4,264,766 | 4/1981 | Fischer . |
| 4,278,651 | 7/1981 | Hales . |
| 4,401,765 | 8/1983 | Craig et al. ........................ 436/533 |

Primary Examiner—Arnold Turk

[57] ABSTRACT

Novel particle reagents for light scattering immunoassays are provided. The particle reagents are high refractive index shell-core polymers covalently bonded to compounds of biological interest or analogs thereof. A method of measuring unknown concentrations of these compounds of biological interest by measuring changes in turbidity caused by particle agglutination or its inhibition is also provided.

3 Claims, No Drawings

COVALENTLY BONDED HIGH REFRACTIVE INDEX PARTICLE REAGENTS AND THEIR USE IN LIGHT SCATTERING IMMUNOASSAYS

CROSS REFERENCE TO RELATED APPLICATION

This application is a Continuation-in-Part of U.S. patent application Ser. No. 315,922, filed Oct. 28, 1981, now U.S. Pat. No. 4,401,765, issued Aug. 30, 1983, which is a Continuation-in-Part of U.S. patent application Ser. No. 298,473, filed Sept. 1, 1981, now abandoned.

TECHNICAL FIELD

This invention relates to novel particle reagents consisting of shell-core particles in which the high refractive index of the core results in high sensitivity to light scattering measurements and the shell contains functional groups to which compounds of biological interest can be covalently bonded. In particular, the compounds of biological interest are antibodies, antigens, and antigen analogs and the particle reagents are designed for use in light scattering immunoassay.

BACKGROUND ART

The agglutination reaction has long been used in visual (semiquantitative) and quantitative assays for a wide variety of bacteria, cell-surface antigens, serum proteins or other analytes of clinical interest. Agglutination results from the reaction of bivalent antibodies with multivalent antigens of interest to produce aggregates which can be detected and/or measured in various ways. Similarly, the same reaction can be utilized for the detection of specific antibodies by the agglutination reaction caused by the addition of the corresponding antigen.

In order to produce large, crosslinked aggregates the number of reactive sites on the antigens must be at least 2. Therefore, when the detection of monovalent haptens was desired, the reaction scheme was modified as follows: A multivalent form of the antigen such as a hapten-protein conjugate was prepared and the hapten present in a sample could compete with its multivalent form for the available binding sites of the antibody thereby reducing the amount of agglutination. This technique is referred to as inhibition of agglutination.

Production of multivalent forms of haptens is old in the art. Frequently the hapten is bonded to a carrier protein as is done in the preparation of immunogens. The stoichiometry of the reaction can be adjusted to place three or more haptens per protein molecule, the exact number being determined by the needs of the particular assay in which the material will be utilized.

Increased sensitivity to visual or instrumental detection of agglutination or its inhibition can be achieved by the use of particle reagents as carriers, rather than soluble proteins or protein conjugates. It has been shown, for example, that antiserum to hen ovalbumin was 2000-fold more sensitive in precipitating hen ovalbumin coated on colloidion particles than in precipitating hen albumin itself; H. N. Eisen, "Immunology", Harper and Row, 1974, page 394.

Antibody particle reagents are also known. A common method for preparation of such reagents is by adsorption of the antibodies onto the surface of suitable adsorbents. Polystyrene-based latex particles have been used extensively for this purpose. For example, U.S. Pat. No. 3,912,805, issued Oct. 14, 1975 to Cayzer, et al., describes an immunological diagnostic reagent wherein antibodies raised to fibrinogen degradation products are adsorbed to latex particles. These reagents, however, are susceptible to desorption during storage or use leading to variations in reagent properties. This, in turn, can adversely affect assay sensitivity and reproducibility.

To overcome the problems of desorption, particle reagents can be prepared by covalent attachment of the compounds of biological interest to the surface of particles. Polystyrene polymers have been modified to include functional groups capable of covalent protein attachment. U.S. Pat. No. 4,064,080, issued Dec. 20, 1977, discloses styrene polymers with terminal aminophenyl groups and proteins attached to them. U.S. Pat. No. 4,181,636, issued Jan. 1, 1980, discloses carboxylated latex polymers coupled to immunologically active materials through a water soluble activating agent and their use as diagnostic reagents in agglutination tests. U.S. Pat. No. 4,210,723, issued July 1, 1980, describes shell-core latex polymer particles of 0.15–1.5 $\mu$m diameter having free epoxy groups on the surface of the particles and the coupling of proteins through these epoxy groups.

Other polymeric systems have also been developed for later attachment of immunologically active materials. U.S. Pat. No. 4,264,766, issued Apr. 28, 1981, discloses latex polymers, having a particle size of 0.01–0.9 $\mu$m and having active groups such as carboxyl and amino groups to which water soluble polyhydroxy compounds can be attached covalently. Through the utilization of activating agents such as carbodiimides, immunologically active materials were attached to the latex particle/polyhydroxy compound carriers to form diagnostically useful reagents.

There is a need for a stable particle reagent which possesses high sensitivity for use in light-scattering agglutination assays and which can be prepared conveniently by the covalent attachment of compounds of biological interest to a particulate carrier.

DISCLOSURE OF THE INVENTION

The particle reagent of this invention has a high refractive index and consists essentially of:
(A) a polymer particle having an inner core and an outer shell wherein the inner core is a polymer having a refractive index of not less than 1.54 as measured at the wavelength of the sodium D line and wherein the outer shell is a polymer of
  (1) an ethylenically unsaturated monomer having a functional group capable of reacting with a compound of biological interest selected from the group consisting of epoxy, carboxyl, amino, hydroxyl and aldehyde,
  (2) optionally, other ethylenically unsaturated monomers in an amount sufficient to produce water insoluble polymer particles, and
  (3) not more than 10 parts by weight of the outer shell of the monomers of the inner core, said outer shell being formed by polymerization in the presence of said inner core; and wherein said polymer particle has an approximate diameter range of 0.03–0.1 $\mu$m and is covalently attached to
(B) a compound of biological interest, its antigen or an analog thereof or its antibody.

The compound of biological interest can be attached to the polymer particle directly or through a proteinaceous material.

A method of this invention for measuring compounds of biological interest comprises the steps of:

(A) incubating
  (1) a particle reagent having high refractive index consisting essentially of:
    (a) a polymer particle having an inner core and an outer shell wherein the inner core is a polymer having a refractive index of not less than 1.54 as measured at the wavelength of the sodium D line and wherein the outer shell is a polymer of
      (i) an ethylenically unsaturated monomer having a functional group capable of reacting with a compound of biological interest selected from the group consisting of epoxy, carboxyl, amino, hydroxyl and aldehyde,
      (ii) optionally, other ethylenically unsaturated monomers in an amount sufficient to produce water insoluble polymer particles, and
      (iii) not more than 10 parts by weight of the outer shell of the monomers of the inner core, said outer shell being formed by polymerization in the presence of said inner core and wherein said polymer particles has an approximate diameter range of 0.03–0.1 $\mu$m and is covalently attached to
    (b) the compound of biological interest or an analog thereof or its antibody;
  (2) a liquid suspected of containing the compound of biological interest; and
  (3) an agglutinating agent; and
(B) photometrically measuring increased particle size resulting from agglutination.

The method of this invention for measuring proteins can be carried out directly without an agglutinating agent with the appropriate complementary particle reagents.

DESCRIPTION OF THE INVENTION

This invention relates to novel particle reagents with optimal properties for use in sensitive light scattering immunoassays. The particle reagents are designed to maximize the sensitivity of the immunoassays by (1) being formed of a core material of high refractive index; (2) possessing a shell material which is capable of covalently binding to compounds of biological interest or analogs thereof; and (3) being of a small particle size for optimal sensitivity in the immunoassays.

By antigen analog or analog of the compound of biological interest is meant any substance or group of substances which share antigenic determinants and, therefore, behaves substantially the same as the compound of biological interest with respect to binding specificity for the antibody to the compound of biological interest.

The light scattering properties of particle suspensions depend on several variables, most importantly the particle size, the refractive indices of the core and the suspension medium, and the wavelength of light used for measurement. Thus, the selection of core material, particle size, and wavelength of detection of the agglutination reaction are all important factors in optimizing assay sensitivity. These factors can be determined by the type of light scattering detection means used.

During visual observation of the agglutination reaction, a broad band of wavelengths, between approximately 400 and 650 nm, is being utilized. Since the light scattering response varies over this wavelength range, the visual observation results in an averaging of the effects of many wavelengths which is less sensitive than choosing the optimum wavelength for a given particle size and refractive index. For particles which are small compared to the wavelength of light, the scattering increases with the inverse 4th power of the wavelength and the magnitude is dependent upon the refractive index. When the wavelength of light approaches an absorption band of the particle, there is an increase of refractive index and thus the light scattering properties are sensitive also to the optical dispersion of the scattering element and the wavelength functionality may exceed the 4th power.

For the turbidimetric detection of particle size change at a given wavelength of measurement it is imperative that the particle size and refractive index be chosen with care since the turbidimetric signal goes through a maximum, producing a double-valued response with little or no sensitivity at the peak. In addition, the slope sensitivity is greater on the small particle size side of the peak than on the large and it increases with increasing refractive index ratio of particle to medium.

For these reasons, small particles of high refractive index with short wavelength detection are preferred for high sensitivity. There is a practical limit in the ultraviolet region for measurement of samples in serum because of light absorption by proteins and other components. Thus, convenient wavelengths are those in excess of approximately 320 nm. Longer wavelengths can be used with less sensitivity. Small particles, that is those with a diameter of less than approximately 0.1 $\mu$m, are preferred because of both increased slope sensitivity and reaction rates. For reasons of stability and synthetic convenience, particle sizes greater than approximately 0.03 $\mu$m are preferred. In general, particle size range of 0.03–0.1 $\mu$m can be utilized in the particle reagent of this invention. Shorter wavelengths, such as 340 nm, give larger signal differences than longer wavelengths, such as 400 nm.

For nephelometric detection, the optimum sensitivity can depend not only on particle size and wavelength, but also on the angle of measurement. Nephelometry refers to the measurement of the light scattered at an angle from the incident beam. The size of the particles for optimum sensitivity will have an angular dependence as well as a wavelength dependence.

Other types of light scattering measurements of the agglutination reaction include particle counting, quasielastic light scattering, autocorrelation spectroscopy, and measurements of the dissymmetry or the polarization of the particles. These types of measurements provide different constraints for the particle reagents.

In all types of measurements, however, the higher the refractive index of the particle at the wavelength of choice, the higher the light scattering signal.

A preferred way of measurement of immunological reactions utilizing the particle reagents of this invention is by turbidity since no special equipment is required other than a spectrophotometer which is generally available in clinical laboratories. The spectrophotometer measures increased absorbance which is due to the increasing particle size resulting from the agglutination reaction. This increased absorbance is a direct measure of the agglutination caused by the analyte or an indirect measure of the agglutination inhibition caused by the analyte. To optimize the turbidity change which occurs during agglutination, it is important to select the particle size with care.

During the agglutination reaction, the effective particle size increases. For sensitive measurements it is therefore important to choose the wavelength at which the signal change for a given particle size change is optimal.

Because of the importance of the refractive index for turbidimetric detection of the agglutination reaction, core materials are restricted to those which will produce acceptable signal changes for the desired assay sensitivity. For analytes in high concentrations (μg/mL range), the choice is not critical, but for analytes in the nanogram/mL range, particles having high refractive index are necessary. Thus core polymers with high aromaticity and high atomic weight substituents are preferred over aliphatic polymers and, in general, polymers of high refractive indices are preferred over polymers with lower refractive indices.

The inner core of the polymer particles can be selected from a large group of materials with high refractive index. Preferred are those materials which can be prepared by emulsion polymerization in a manner so that the final particle size is controllable and is substantially uniform. Typical polymers utilized in the inner core of the polymer particles have refractive indices greater than 1.54 (at the Na D line, 569 nm) and are listed in Table 1. Since the refractive index is a function of wavelength, the scattering properties will be dependent upon the wavelength of measurement. In general, the refractive index is greater at shorter wavelengths.

TABLE 1
REFRACTIVE INDICES OF POLYMERS

| Polymer | $n_D$ |
|---|---|
| Cellulose | 1.54 |
| Poly(vinyl chloride) | 1.54–1.55 |
| Urea-formaldehyde resin | 1.54–1.56 |
| Poly(sec-butyl α-bromoacrylate) | 1.542 |
| Poly(cyclohexyl α-bromoacrylate) | 1.542 |
| Poly(2-bromoethyl methacrylate) | 1.5426 |
| Poly(dihydroabietic acid) | 1.544 |
| Poly(abietic acid) | 1.546 |
| Poly(ethylmercaptyl methacrylate) | 1.547 |
| Poly(N—allyl methacrylamide) | 1.5476 |
| Poly(1-phenylethyl methacrylate) | 1.5487 |
| Poly(vinylfuran) | 1.55 |
| Poly(2-vinyltetrahydrofuran) | 1.55 |
| Poly(vinyl chloride) + 40% tricresyl phosphate | 1.55 |
| Epoxy resins | 1.55–1.60 |
| Poly(p-methoxybenzyl methacrylate) | 1.552 |
| Poly(isopropyl methacrylate) | 1.552 |
| Poly(p-isopropylstyrene) | 1.554 |
| Poly(chloroprene) | 1.554–1.55 |
| Poly(oxyethylene)-α-benzoate-ω-methacrylate) | 1.555 |
| Poly(p,p'-xylylenyl dimethacrylate) | 1.5559 |
| Poly(1-phenylallyl methacrylate) | 1.5573 |
| Poly(p-cyclohexylphenyl methacrylate) | 1.5575 |
| Poly(2-phenylethyl methacrylate) | 1.5592 |
| Poly(oxycarbonyloxy-1,4-phenylene-1-propyl-butylidene-1,4-phenylene) | 1.5602 |
| Poly[1-(o-chlorophenyl)ethyl methacrylate] | 1.5624 |
| Poly(styrene-co-maleic anhydride) | 1.564 |
| Poly(1-phenylcyclohexyl methacrylate) | 1.5645 |
| Poly(oxycarboxyloxy-1,4-phenylene-1,3-dimethylbutylidene-1,4-phenylene) | 1.5671 |
| Poly(methyl α-bromoacrylate) | 1.5672 |
| Poly(benzyl methacrylate) | 1.5680 |

TABLE 1-continued
REFRACTIVE INDICES OF POLYMERS

| Polymer | $n_D$ |
|---|---|
| Poly[2-(phenylsulfonyl)ethyl methacrylate] | 1.5682 |
| Poly(m-cresyl methacrylate) | 1.5683 |
| Poly(styrene-co-acrylonitrile) | 1.57 |
| (ca. 75/25) | 1.57 |
| Poly(oxycarbonyloxy-1,4-phenyleneisobutylidene-1,4-phenylene) | 1.5702 |
| Poly(o-methoxyphenyl methacrylate) | 1.5705 |
| Poly(phenyl methacrylate) | 1.5706 |
| Poly(o-cresyl methacrylate) | 1.5707 |
| Poly(diallyl phthalate) | 1.572 |
| Poly(2,3-dibromopropyl methacrylate) | 1.5739 |
| Poly(oxycarbonyloxy-1,4-phenylene-1-methylbutylidene-1,4-phenylene) | 1.5745 |
| Poly(oxy-2,6-dimethylphenylene) | 1.575 |
| Poly(oxyethyleneoxyterephthalate) | 1.575 |
| Poly(vinyl benzoate) | 1.5775 |
| Poly(oxycarbonyloxy-1,4-phenylene-butylidene-1,4-phenylene) | 1.5792 |
| Poly(1,2-diphenylethyl methacrylate) | 1.5816 |
| Poly(o-chlorobenzyl methacrylate) | 1.5823 |
| Poly(oxycarbonyloxy-1,4-phenylene-sec-butylidene-1,4-phenylene) | 1.5827 |
| Poly(oxypentaerythritoloxyphthalate) | 1.584 |
| Poly(m-nitrobenzyl methacrylate) | 1.5845 |
| Poly(oxycarbonyloxy-1,4-phenylene-isopropylidene-1,4-phenylene) | 1.5850 |
| Poly(N—2-phenylethyl methacrylamide) | 1.5857 |
| Poly(4-methoxy-2-methylstyrene) | 1.5868 |
| Poly(o-methylstyrene) | 1.5874 |
| Poly(styrene) | 1.59–1.592 |
| Poly(oxycarbonyloxy-1,4-phenylene-cyclohexylidene-1,4-phenylene) | 1.5900 |
| Poly(o-methoxystyrene) | 1.5932 |
| Poly(diphenylmethyl methacrylate) | 1.5933 |
| Poly(oxycarbonyloxy-1,4-phenylene-ethylidene-1,4-phenylene) | 1.5937 |
| Poly(p-bromophenyl methacrylate) | 1.5964 |
| Poly(N—benzyl methacrylamide) | 1.5965 |
| Poly(p-methoxystyrene) | 1.5967 |
| Hard rubber (32% S) | 1.6 |
| Poly(vinylidene chloride) | 1.60–1.63 |
| Poly(sulfides) | 1.6–1.7 |
| Poly(o-chlorodiphenylmethyl methacrylate) | 1.6040 |
| Poly[oxycarbonyloxy-1,4-(2,6-dichloro)phenylene-isopropylidene-1,4-(2,6-dichloro)phenylene)] | 1.6056 |
| Poly[oxycarbonyloxybis{1,4-(3,5-dichlorophenylene)}] | 1.6056 |
| Poly(pentachlorophenyl methacrylate) | 1.608 |
| Poly(o-chlorostyrene) | 1.6098 |
| Poly(phenyl α-bromoacrylate) | 1.612 |
| Poly(p-divinylbenzene) | 1.6150 |
| Poly(N—vinylphthalimide) | 1.6200 |
| Poly(2,6-dichlorostyrene) | 1.6248 |
| Poly(β-naphthyl methacrylate) | 1.6298 |
| Poly(α-naphthyl carbinyl methacrylate) | 1.63 |
| Poly(sulfone) | 1.633 |
| Poly(2-vinylthiophene) | 1.6376 |
| Poly(αnaphthyl methacrylate) | 1.6410 |
| Poly(oxycarbonyloxy-1,4-phenylene-diphenylmethylene-1,4-phenylene) | 1.6539 |
| Poly(vinyl phenyl sulfide) | 1.6568 |
| Butylphenol-formaldehyde resin | 1.66 |
| Urea-thiourea-formaldehyde resin | 1.660 |
| Poly(vinylnaphthalene) | 1.6818 |
| Poly(vinylcarbazole) | 1.683 |
| Naphthalene-formaldehyde resin | 1.696 |
| Phenol-formaldehyde resin | 1.70 |
| Poly(pentabromophenyl methacrylate) | 1.71 |

Not all of the polymers listed above can be utilized as the inner core for the particle reagents of this invention since there are additional criteria to be applied to the selection of core monomer materials. Cellulose, for example, is not readily prepared as uniform particle size spheres. Condensation polymers are also not useful since the polymerization process does not lead to spherical particles of the type which can be obtained by emulsion polymerization. Some thermoplastic polymers such as poly(oxyethylene-oxyterephthalate) and some thermosetting resins of the urea-formaldehyde type are not suitable.

The monomers of interest are those which contain vinyl or allyl groups in addition to substituents such as halides, aromatic, heterocyclic, unsaturated or carbocyclic groups which impart high refractivity.

Polymer particles useful for the preparation of the particle reagents of this invention can be prepared preferentially by emulsion polymerization. Staged emulsion polymerization can lead to a core/shell polymer approximating the desired refractive index of not less than $n_D=1.54$. To obtain a polymer of desired refractive index, it is preferred that the shell polymer not exceed approximately 10 parts by weight of the polymer particle.

A convenient way to control particle size of the polymer particles is to first prepare a seed emulsion whose size can be controlled by the amount of surfactant used. After preparation of the seed emulsion, additional monomer and surfactant can be added at a controlled rate to increase the size of the particles in the seed emulsion.

The outer shell polymer of the polymer particle can be prepared from a wide range of ethylenically unsaturated monomers having functional groups capable of reacting with compounds of biological interest. Optionally, the outer shell can also contain other ethylenically unsaturated monomers. The attachment of the shell polymer to the core can be accomplished by graft polymerization of the functional monomer to the residual ethylenically unsaturated groups in the core polymer or the functional monomer can be polymerized around the core to produce a contiguous shell. Preferred monomers include those containing an epoxy group such as glycidyl methacrylate, glycidyl acrylate, vinyl glycidyl ether, and methallyl glycidyl ether. Other functional groups include carboxyl, hydroxyl, amino, and aldehyde.

It is preferable to carry the conversion of the core monomer(s) to substantial completion so that the shell polymer is a homopolymer or a copolymer of known composition rather than a copolymer of unknown composition. Conversions in excess of 98% can be attained by increasing the temperature of the core emulsion to approximately 95° C. at the end of the polymerization. To further reduce the probability of producing particles whose surface is a copolymer of unknown composition, the shell monomer can be added gradually rather than batchwise. In such a manner, the residual core monomer(s) can be consumed during the early stages of the shell polymer formation. When the monomer utilized is one which contains an epoxy group, it is preferred that the shell polymer be a homopolymer although, as a practical matter, monomers of the inner core, up to 10 parts by weight of the outer shell, can be present.

In the case of the shell monomers containing hydroxyl, amino, aldehyde or carboxylic acid groups, care must be taken to avoid the formation of water soluble polymers. Thus, for example, acrolein or methacrylic acid cannot be utilized alone to form a homopolymer shell structure. They can be copolymerized, however, with additional monomers in amounts sufficient to produce water insoluble polymer particles.

It is also possible to modify the outer shell polymer by subsequent treatment to produce a surface capable of covalent attachment by alternative chemical techniques. For example, an epoxy group can be hydrolyzed to form a diol compound capable of reacting with cyanogen bromide which can act as a coupling agent for amine groups in proteins.

Aldehydes can react directly with amines to form a Shiff's base which can be subsequently reduced to form a covalent link. Alternatively, the aldehyde can be oxidized to an acid and carbodiimide can be used for subsequent reaction with amines to form an amide link.

The outer shell is preferably a homopolymer but can contain not more than 10 parts, preferably not more than 5 parts, and even more preferably not more than 2 parts, by weight of the outer shell of the monomers of the inner core. These monomers can be the residual monomers from the polymerization of the inner core.

The particle reagents of this invention can contain several different functional shell materials. A preferred one contains epoxy groups which can be conveniently utilized for the covalent attachment of compounds of biological interest such as haptens, antibodies, proteins or hapten-protein conjugates. Such a reaction results in the particle reagents of this invention.

The preparation of the particle reagents can be carried out as follows: The hapten or proteinaceous material, for example, can be adsorbed onto the surface of the polymer particle, followed by the reaction of the functional group, for example, the epoxide group, under suitable pH conditions, with the complementary functional group of the hapten or the proteinaceous material. A protein which does not interfere with the assay such as human serum albumin can also be included to bind and to block unoccupied sites on the particle surface. Other such blocking agents incude mercaptoethanol, mercaptopropionic acid, cysteine and soluble polymers having amino-functional groups attached. Any unreacted material is then separated from the particle reagent. The conditions of the reaction are such that there should be no substantial crosslinking of particles occurring. That would result in nonuniform reagent particles and unpredictable turbidity changes during the subsequent immunoassay.

There can be two ways of preparing a particle reagent which contains a compound of biological interest or analog thereof covalently attached through a proteinaceous material. The compound of biological interest, such as a hapten, can first be attached to the carrier protein and then attached to the polymer particle. Alternatively, the protein can first be attached to the polymer particle and then the hapten can be attached to the protein. The second approach has the advantage of using the same protein-particle reagent for the synthesis of particle reagents having a variety of compounds of biological interest attached to them. It is also possible to attach the compound of biological interest or its analog directly to the polymer particle.

The surface coverage of the polymer particle by a hapten or proteinaceous material, that is the ratio of the polymer particles to compounds of biological interest, can be varied by reaction time, by dilution of the compounds of biological interest with an inactive diluent or by an additive which aids in the dispersion of the particles. While complete coverage can yield fast agglutination rates, lesser surface coverage can be important in increasing assay sensitivity.

The resulting particle reagent can be suspended in a substantially aqueous medium which can further contain buffer, serum components and surfactants to yield a monodispersed particle reagent for use in light scattering immunoassay.

The present invention is further concerned with an immunologically active, stable particle reagent for use in sensitive light scattering immunoassays for measuring compounds of biological interest. The types of assays include a wide variety of substances in biological fluids, cell and tissue extracts for which an immunological counter reactant can be produced. The compounds of biological interest include serum, plasma, salivary, urinary or milk proteins; drugs, vitamins, hormones, enzymes, antibodies, polysaccharides, bacteria, protozoa, fungi, viruses; cell and tissue antigens and other blood cell or blood fluid substances. Of special interest are those substances for which a quantitative determination is required for the assessment of disease state, as well as various drugs.

The immunoassay can be designed in a variety of ways depending on the type of analyte and the sensitivity required.

For analytes in relatively high concentration such as certain serum proteins, appropriate antibody particle reagents can be used in a direct particle enhanced turbidimetric immunoprecipitation assay. The method of this invention provides increased detectability over conventional immunoprecipitation techniques, corresponding savings in reagent costs, and allows the use of smaller patient sample volumes. Conversely, for the detection of circulating antibodies of interest, the counter reactive antigen or antibody particle reagent can be used in a direct assay.

The inhibition immunoassay method of this invention also requires, in addition to the particle reagent, a bi- or multifunctional agent, hereinafter referred to as an agglutinating agent to cause the agglutination of the particle reagent. It is this agglutination which can be inhibited by the compound of biological interest. The agglutinating agent can be an antibody to the compound of biological interest or its analog or a particle reagent based on a polymer particle, as described above, covalently attached to an antibody of the compound of biological interest. These agglutinating agents are utilized in those situations where the particle reagent utilized in the method contains a covalently attached compound of biological interest or analog thereof.

The agglutinating agent can also be a multivalent conjugate of the compound of biological interest and a protein. Such a conjugate is utilized in situations where the particle reagent utilized in the method of this invention contains a covalently attached antibody of the compound of biological interest.

For the measurement of haptens, several different assay configurations can be utilized. In one such configuration, antigenic particle reagents can be prepared (either hapten-particle or hapten-protein-particle reagents) and the inhibition of the reaction of these particles with antibodies by the compound of biological interest is determined. The reaction can be performed by direct competition between the particle and the patient hapten for the antibody or by sequential reaction of the hapten with antibody followed by addition of the antigen particle reagent. This configuration can also be utilized for the measurement of certain serum proteins.

Antigenic particle reagents can be prepared from analogs of compounds of biological interest; for example oubain can be utilized in particle reagents for the detection of digoxin and fibrinogen can be similarly utilized in assays for fibrin degradation products and fibrinogen degradation products.

Another assay configuration for haptens utilizes antibody particle reagents wherein the agglutination of the antibody particle reagents with soluble multi-haptenic protein conjugates is inhibited by the analyte. Such an assay can also be performed in a competitive or sequential mode. In yet another assay, both antibody and antigenic particle reagents can be present, of the same or differing sizes, and the inhibition by haptens can be performed in a competitive or sequential mode.

The agglutination reaction during the method of this invention can be accelerated by the presence of an agglutinating accelerator. Such an accelerator can be a polyethylene glycol or a surfactant such as sodium dodecyl sulfate. This latter is particularly useful in an assay for digoxin utilizing a digoxin-HSA-particle reagent.

The following examples are illustrative of the invention.

EXAMPLE 1

Preparation of Polystyrene/Polyglycidyl Methacrylate Shell-Core Polymer Particle (a) A 3-liter roundbottomed flask, equipped with a stirrer and a thermostated heating mantle, is used for the polymerization which is carried out at 70° C. under a nitrogen atmosphere. The seed emulsion is prepared by adding 50 mL of styrene to 2 L of water containing 6 g of "Gafac" RE 610 (an anionic surfactant available from GAF Corp.) and 2 g of potassium persulfate. After one half of one hour, a monomer feed, consisting of 400 mL of styrene, 4 mL allyl methacrylate, and 1.5 g of Aerosol OT-100 (a dioctyl sodium sulfosuccinate, available from American Cyanamid Co.), is started at the rate of 4 mL/min. After the feed is completed, the emulsion is kept at 70° C. for one hour to insure complete conversion of the styrene. The final solids content is 15.9%, the particle size of the core polystyrene emulsion (determined by turbidity measurements at 546 nm) is 0.067 $\mu$m, and the surface tension (determined by a tensiometer using the du Nouy Ring method) is 65 dynes/cm$^2$.

(b) A 300-mL roundbottomed flask is used for the preparation of the shell-core polymer. The polymerization is carried out at 80° C. under a nitrogen atmosphere. 200 mL of the core polystyrene emulsion (Example 1a) is added to 50 mL of water containing 0.2 g of potassium persulfate and 0.2 g of anhydrous potassium carbonate, followed by the addition of 3.9 mL of glycidyl methacrylate at a rate of 0.1 mL/min. After 45 min the mixture is cooled. The final shell-core polymer has a particle size of 0.069 $\mu$m.

EXAMPLE 2

Preparation of Polystyrene/Polyglycidyl Methacrylate Shell-Core Polymer Particle (a) A 3-liter roundbottomed flask, equipped with a stirrer and a thermostated heating mantle, is used for the polymerization. Styrene is purified prior to polymerization by passing through a column packed with basic alumina. The polymerization is performed at 70° C. under a slow stream of nitrogen.

The polymerization is started by adding 45 mL of styrene, 5 mL of ethylene glycol dimethacrylate, 50 mL of a 30% solution of sodium dodecyl sulfate in water, and 2 g of potassium persulfate to 2 L of deionized water. This mixture is allowed to polymerize at 70° C. for 20 min. At this point, the particle size is 0.021 μm and the surface tension is 38.8 dynes/cm$^2$, indicating that substantially all of the surfactant is utilized for particle stabilization.

The particles are then grown to a final size of 0.043 μm by gradually adding 400 mL of styrene and 10 g of "Aerosol" OT-100 at a rate of 4 mL/min. The final size is predicted to be 0.044 μm, based on the initial particle size and the volume of added styrene.

590 mL of seed emulsion, prepared above, is added to 1510 mL of deionized water containing 1.5 g of potassium persulfate and is heated to 70° C. When the mixture reaches 70° C., 340 mL of styrene and 3.4 g of "Aerosol" OT-100 are added at a rate of 4 mL/min. When the feed is complete, the temperature is increased to 95° C. for 0.5 h to insure high conversion of the monomers. The conversion is 98.4% complete, as measured by gas chromatography of an ether extract of the emulsion. The final core size is 0.070 μm. (The predicted value is 0.069 μm, calculated from the initial size and the volume of styrene added.)

(b) 200 mL of water, containing 2 g of potassium carbonate and 2 g of potassium persulfate, is added to the core polymer prepared in (a) above and the reaction temperature is adjusted to 80° C. 50 mL of glycidyl methacrylate is then added at a rate of 1.5 mL/min. A total of 45 min is allowed for the shell polymerization. The final particle size is 0.71 μm and the glycidyl methacrylate conversion is 97.3% (using a gas chromatographic measurement as with the styrene). The final styrene conversion appears to be complete since no styrene is detectable by chromatography.

EXAMPLE 3

Preparation of Polyvinyl Carbazole/Polyglycidyl Methacrylate Shell-Core Polymer Particle A 300-mL roundbottomed flask, equipped with a distillation head and a mechanical stirrer, is utilized. 200 mL of water containing 0.5 g of potassium persulfate, 0.5 g of trisodium phosphate dodecahydrate, and 1.5 g of sodium dodecyl sulfate are heated to 70° C. under a nitrogen atmosphere. A seed emulsion is formed by adding 4.5 mL of styrene and 0.5 mL of ethylene glycol dimethacrylate. After 30 min the seed emulsion has a particle size of 0.021 μm and pH of 8.5. A solution of 20 g of vinyl carbazole and one gram of "Aerosol" OT-100 in 10 mL of dichloromethane is then added at a rate of 0.1 mL/min. The dichloromethane is removed by distillation as soon as it is added. After the core emulsion is complete, 0.1 g of potassium persulfate in 10 mL of water is added, and then 2.5 mL of glycidyl methacrylate is added at a feed rate of 0.1 mL/min. 45 min is allowed for the polymerization. The final particle size is 0.041 μm. The final solids content is 10.5%.

EXAMPLE 4

Preparation of Polystyrene/Polyglycidyl Methacrylate Shell-Core Polymer Particle (a) The procedure of Example 1(a) is utilized as follows. To 2 L of water containing 2 g of azobisisobutyramidine hydrochloride are added 50 mL of styrene and 2 g of cetyl trimethyl ammonium bromide and allowed to polymerize for 30 min. Then, a mixture of 200 mL of styrene and 2 mL of allyl methacrylate is added at a rate of 4 mL/min. After the addition of 100 mL, and again at the completion of the addition, 0.75 g of cetyl trimethyl ammonium bromide is added. The final solids content is 10.5% and the particle size is 0.106 μm.

(b) A mixture of 200 mL of the core emulsion prepared in Example 4(a) above, 0.2 g of azobisisobutyramidine hydrochloride, and 0.2 g of sodium acetate (anhydrous) dissolved in 10 mL of water is heated to 70° C. under a nitrogen atmosphere. After the temperature is stabilized, 3 mL of glycidyl methacrylate is added at a rate of 0.1 mL/min. 45 min is allowed for the polymerization. The final emulsion has a surface tension of 48.5 dynes/cm$^2$.

EXAMPLE 5

Measurement of Fibrinogen (a) Attachment of Fibrinogen to Polymer Particles

A solution containing 25 mg of fibrinogen, 225 mg of human serum albumin (HSA), and 6 mL of polymer particle latex prepared as in Example 4 above in a total volume of 250 mL of 0.015 M tris buffer, pH 8.0, was incubated for 3 days at 4° C. The particles were separated by centrifugation and resuspended in 250 mL of 0.015 M phosphate buffer, pH 8.0, containing 0.1% (w/v) HSA. The mixture was warmed to 70° C. for one hour and then cooled to 4° C. The particles were again separated by centrifugation and resuspended in 240 mL of 0.015 M phosphate buffer, pH 7.8, containing 0.1% (w/v) sodium dodecyl sulfate (SDS). They were again separated by centrifugation and resuspended in 325 mL of 0.015 M glycine buffer, pH 7.7, containing 0.1% (w/v) HSA, 0.1% (w/v) lithium dodecyl sulfate (LDS), and 0.1% (w/v) thimerosal.

(b) Assay for Fibrinogen

The assay was performed at 37° C. on the aca ™ discrete clinical analyzer (E. I. du Pont de Nemours and Company). Standards were prepared by adding purified human fibrinogen (available from Kabi Diagnostica) to normal human serum; the zero standard contained 5.0% (w/v) HSA in water. 200-μL samples of each of the standards were added to 4.80 mL of 0.15 M phsophate buffer, pH 7.8, in the filling station of the instrument. 0.05 mL of fibrinogen polymer particle latex prepared in (a) above, 0.125 g PEG-6000, 5 mg SDS, and 6 mg dithioerythritol (DTE) were added at breaker-mixer I, followed by the addition of 0.019 mL of rabbit anti-human fibrinogen antiserum (available from Cappel Laboratories) 3.5 minutes later. The change in turbidity was measured at 340 nm 39 seconds and 56 seconds after antiserum addition. Table 2 shows the rate of change in abosrbance at 340 nm in milliabsorbance units/minute (mAu/min) as a function of fibrinogen concentration.

TABLE 2

| Inhibition of Turbidity by Fibrinogen | |
|---|---|
| Fibrinogen Concentration (μg/mL) | Rate (mAu/min at 340/nm) |
| 0 | 123 |
| 10 | 96 |
| 20 | 71 |
| 40 | 58 |
| 60 | 49 |
| 100 | 37 |

EXAMPLE 6

Measurement of Fibrinogen Degradation Products

The assay was performed as described in Example 5(b) above, except that the standards were prepared by adding fibrinogen degradation products to normal human serum. Fibrinogen degradation products were prepared by degrading 200 mg of purified fibrinogen with 25 CU (casein units) of plasminogen, activated by 500 U of streptokinase at 37° C. After 1 hour, the reaction was terminated by the addition of soybean trypsin inhibitor to a final concentration of 1 mg/mL. The zero level standard consisted of 5% (w/v) HSA in water.

Table 3 shows the rate of change in absorbance at 340 nm as a function of fibrinogen degradation products concentration.

TABLE 3
Inhibition of Turbidity by Fibrinogen Degradation Products

| Fibrinogen Degradation Products ($\mu$g/mL) | Rate (mAu/min at 340/nm) |
|---|---|
| 0 | 124 |
| 10 | 96 |
| 20 | 75 |
| 40 | 66 |
| 60 | 60 |
| 100 | 50 |

Since fibrinogen and its degradation products share antigenic determinants, it is possible to use polymer particles with attached fibrinogen for the measurement of fibrinogen degradation products.

EXAMPLE 7

Measurement of Fibrin Degradation Products

The assay was performed as described in Example 5(b) above, except that the standards were prepared by adding fibrin degradation products to normal human serum. Fibrin degradation products were prepared by allowing a fibrin clot to form from 200 mg of purified fibrinogen and then degrading it with 5 Sigma units of human plasmin at 35° C. for 96 hours. The zero level standard was water. Table 4 shows the rate of change in absorbance at 340 nm as a function of fibrin degradation products concentration.

TABLE 4
Inhibition of Turbidity by Fibrin Degradation Products

| Fibrinogen Degradation Products ($\mu$g/mL) | Rate (mAu/min at 340/nm) |
|---|---|
| 0 | 142 |
| 20 | 108 |
| 40 | 84 |
| 60 | 61 |
| 80 | 56 |
| 100 | 37 |

Since fibrinogen and fibrin degradation products share antigenic determinants, it is possible to use polymer particles with attached fibrinogen for the measurement of fibrin degradation products.

We claim:

1. A method for measuring compounds of biological interest comprising the steps of
   (A) incubating
   (1) a particle reagent having high refractive index consisting essentially of:
      (a) a polymer particle having an inner core and an outer shell wherein the inner core is a polymer having a refractive index of not less than 1.54 as measured at the wavelength of the sodium D line and wherein the outer shell is a polymer of
         (i) an ethylenically unsaturated monomer having a functional group capable of reacting with a compound of biological interest selected from the group consisting of epoxy, carboxyl, amino, hydroxyl and aldehyde,
         (ii) optionally, other ethylenically unsaturated monomers in an amount sufficient to produce water insoluble polymer particles, and
         (iii) not more than 10 parts by weight of the outer shell of the monomers of the inner core, said outer shell being formed by polymerization in the presence of said inner core and wherein said polymer particles has approximate diameter range of 0.03–0.1 $\mu$m;
      and is covalently attached to
      (b) an analog of a compound of biological interest;
   (2) a liquid suspected of containing the compound of biological interest; and
   (3) an agglutinating agent; and
   (B) photometrically measuring increased particle size resulting from agglutination.

2. The method of claim 1 wherein during the incubation step (A) there is also present an agglutinating accelerator.

3. The method of claim 2 wherein the agglutinating accelerator is selected from the group consisting of polyethylene glycol and sodium dodecyl sulfate.

* * * * *